(12) United States Patent  
Trotta et al.

(10) Patent No.: US 11,844,838 B2  
(45) Date of Patent: Dec. 19, 2023

(54) CROSS-LINKED MALTODEXTRINS FOR THE ORAL DELIVERY OF BIOLOGICAL ACTIVES

(71) Applicant: ROQUETTE FRERES, Lestrem (FR)

(72) Inventors: Francesco Trotta, Asti (IT); Roberta Cavalli, Alessandria (IT); Fabrizio Caldera, Alice Castello (IT); Monica Argenziano, Turin (IT); Maria Tannous, Safra (LB)

(73) Assignee: ROQUETTE FRERES, Lestrem (FR)

( * ) Notice: Subject to any disclaimer, the term of this patent is extended or adjusted under 35 U.S.C. 154(b) by 67 days.

(21) Appl. No.: 16/630,784

(22) PCT Filed: Jul. 11, 2018

(86) PCT No.: PCT/EP2018/068743  
§ 371 (c)(1),  
(2) Date: Jan. 13, 2020

(87) PCT Pub. No.: WO2019/011964  
PCT Pub. Date: Jan. 17, 2019

(65) Prior Publication Data  
US 2021/0085795 A1    Mar. 25, 2021

(30) Foreign Application Priority Data

Jul. 12, 2017  (EP) .................................... 17290094

(51) Int. Cl.  
*A61K 47/36*  (2006.01)  
*A61P 3/10*   (2006.01)  
*A61K 9/00*   (2006.01)  
*A61K 38/28*  (2006.01)

(52) U.S. Cl.  
CPC ............ *A61K 47/36* (2013.01); *A61K 9/0053* (2013.01); *A61K 38/28* (2013.01); *A61P 3/10* (2018.01)

(58) Field of Classification Search  
None  
See application file for complete search history.

(56) References Cited

U.S. PATENT DOCUMENTS

2010/0196542 A1   8/2010  Boursier  
2015/0118280 A1*  4/2015  Barzilay ................ A23K 20/20  
                                              424/442

FOREIGN PATENT DOCUMENTS

WO   WO-2015111062 A1 *  7/2015  ......... A61K 38/2278  
WO      2016004974 A1    1/2016

OTHER PUBLICATIONS

Korang-Yeboah et al., "Abstract 4518: PCL/Maltodextrin delivered ID4 maintains its tumor suppressor role" Cancer Chemistry, Proceedings: AACR 104th Annual Meeting 2013; Apr. 6-10, 2013 DOI: 10.1158/1538-7445.AM2013-4518 (Year: 2013).*  
Bernocchi, B., "Porous maltodextrin nanoparticles for the intranasal delivery of vaccines" https://tel.archives-ouvertes.fr/tel-01480950 (Year: 2017).*

(Continued)

*Primary Examiner* — Eric Olson  
(74) *Attorney, Agent, or Firm* — Troutman Pepper Hamilton Sanders LLP (Rochester)

(57) ABSTRACT

The invention relates to oral administration of biological actives, in particular of insulin, comprising the use of a cross-linked starchy material as a delivery system.

13 Claims, 2 Drawing Sheets

(56) References Cited

OTHER PUBLICATIONS

Mahkam et al., "Starch-based polymeric carriers for oral-insulin delivery" Journal of Biomedical Materials Research Part A vol. 92A pp. 1392-1397 (Year: 2009).*
International Search Report and Written Opinion for PCT/EP2018/068743, dated Nov. 28, 2018.

* cited by examiner

CROSS-LINKED MALTODEXTRINS FOR THE ORAL DELIVERY OF BIOLOGICAL ACTIVES

This application is a national stage application under 35 U.S.C. § 371 of PCT Application No. PCT/EP2018/068743, filed Jul. 11, 2018, which claims the priority benefit of EP Patent Application No. 17290094.6, filed Jul. 12, 2017.

The invention relates to oral administration of biological actives, in particular of insulin, comprising the use of a cross-linked starchy material as a delivery system.

DISCUSSION OF THE PRIOR ART

The gastro-intestinal tract presents a mucosal surface that separate internal structures from the external world which is composed of a single layer of polarized epithelial cells. Despite their delicate nature, these epithelial sheets provide a formidable barrier to the casual and unregulated uptake of most materials that the body is exposed to through ingestion.

While protecting the body from the many toxins and pathogens that the body is exposed to on a daily basis, this barrier also prevents the efficient uptake of biopharmaceuticals including peptides, proteins, and DNA- and RNA-based drugs.

This is even more difficult when it comes to the oral route. Before reaching the systemic circulation, biopharmaceuticals have to retain their intact structure, integrity and conformation through the stomach and intestine. However biopharmaceuticals are particularly sensitive to the gastro-intestinal tract environment, mainly due to the high gastric acidity, and to the presence of hydrolyzing enzymes.

Moreover, the large molecular size and/or hydrophilic nature of biopharmaceuticals like proteins prevent them from diffusing across the mucin barrier, a thick layer of mucus coating the gastro-intestinal epithelium.

This results that the parenteral route is commonly used for the administration of biological actives.

However such administration routes have the drawbacks inherent to their invasive nature. They provoke local pain, discomfort, irritation, needlestick injuries and risk of infection.

Among well-known biological actives currently administrated parenterally, mention may be made of insulin, which requires subcutaneous injections This systemic administration route of insulin further has the disadvantage that only a small proportion of insulin can reach the liver successfully for its own physiological action. Retention of insulin in the peripheral circulation can lead to peripheral insulin resistance and immunogenicity. Hyperinsulinemia can also occur when injected insulin works at the wrong targets, causing hypertension, cardiovascular diseases, weight gain and peripheral edema.

It follows from the above that the delivering of insulin (and more generally of biological actives) through the oral route would have several advantages over systemic administration routes. It could notably help in improving patient's comfort and compliance to the therapy.

Recently, it was interestingly proposed in patent application ITBO20120710, to use cyclodextrin cross-linked by pyromellitic dianhydride as a delivery system for oral administration of insulin. It was showed that insulin loaded in such cross-linked material, was not only capable of remaining intact into the gastrointestinal tract, but was also capable of crossing its membrane and to enter the plasmatic compartment.

However, these delivery systems still needed to be improved. The oral taking of insulin by way of this delivery system provokes a high peak of blood insulin after administration which can lead to harmful hypoglycemia. Moreover, blood insulin decreases quite quickly after ingestion, meaning that repeated administration are required in order to maintain the blood insulin at a satisfying level over time.

There was thus still an unsatisfied need for an improved and safe delivery system for oral administration of insulin, and more generally of biological actives. More specifically, there was still a need for a delivery system able to improve the pharmacokinetic behavior of those biological actives.

OBJECTIVE

This is thus an object of the present invention to provide a safe and efficient system for the oral delivery of biological actives, in particular of insulin.

In particular, it is an object of the present invention to provide a delivery system capable of improving the pharmacokinetic properties and bioavailability of biological actives administrated orally.

PRESENTATION OF THE INVENTION

The inventors successfully remedied the drawbacks of the technologies of prior art, especially of the cross-linked cyclodextrins of patent application ITBO20120710, by developing a new and safe system for the non-parenteral delivery of biological actives, associated with great bioavailability and pharmacokinetic profile of the latter.

The delivery system of the invention is characterized by the fact that it uses a cross-linked maltodextrin.

The delivery system according to the invention is able to markedly increase the pharmacokinetic profile of active proteins after oral administration. This is apparent from the Examples below in which the inventors demonstrated that oral administration of insulin by way of the delivery system of the invention can provide long-lasting effect, especially longer than the one obtained with the cross-linked cyclodextrins of patent application ITBO20120710. In particular, the inventors showed that the delivery system of the invention advantageously provokes slower release of insulin. This means that for the same amount of insulin administered, the delivery system of the invention allows insulin release during a longer period of time, and can thus be active longer. Moreover, the peak of blood insulin observed after oral administration is 2 times lower than the one observed with the delivery system of prior art. The result is that the delivery system of the invention is safer, as there are less risks of post-administration hypoglycemia.

The delivery system of the invention also has the advantage of being based on starchy material which is a bio-based material which can be easily obtained and transformed, and which is well-tolerated.

BRIEF DESCRIPTION OF THE INVENTION

The invention thus first relates to a composition intended for oral administration of a biological active, comprising a cross-linked maltodextrin and an efficient quantity of said biological active.

The invention also related to a method for the preparation of a composition according to the invention, comprising a step of loading a cross-linked maltodextrin with an efficient quantity of a biological active.

The invention also relates the use of a cross-linked maltodextrin, for the oral delivery of a biological active.

The invention also related to a method for treating an individual, comprising oral administration of a composition according to the invention.

In a further aspect the invention relates to a long-lasting release oral formulation, i.e. a prolonged release oral formulation, comprising the composition of the invention and suitable excipients. The oral formulation can be a medicament or a veterinary product or a product selected from the group consisting a cosmetic product, a food and a nutraceutical product.

DETAILED DESCRIPTION OF THE INVENTION

Figure 1:
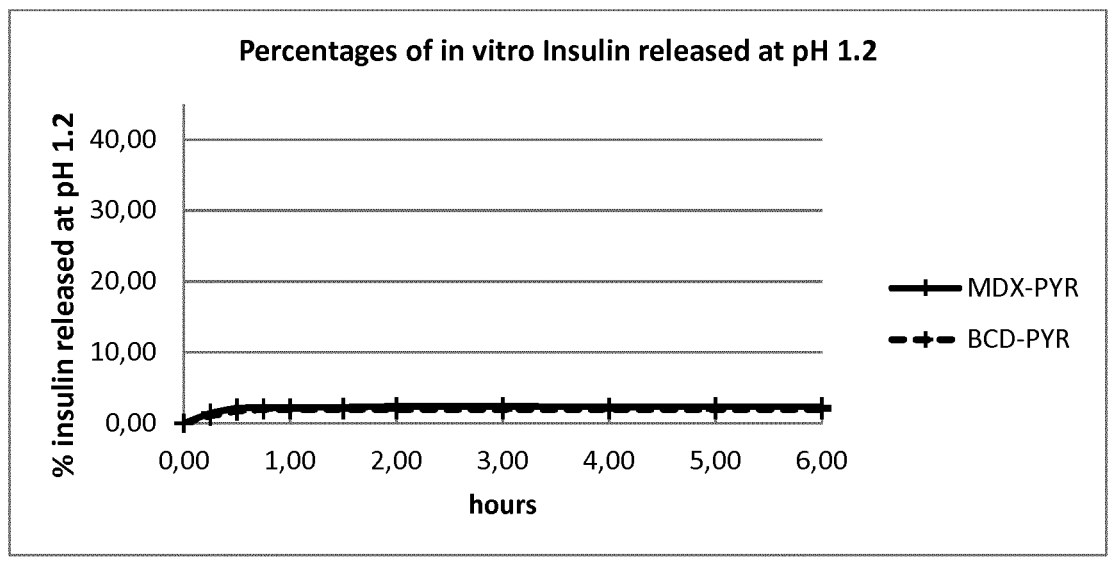
FIG. 1: Percentages of in vitro insulin released from different delivery systems at pH 1.2 over the time.

The instant invention thus relates to the use of a cross-linked maltodextrin for the oral delivery of a biological active, in particular of insulin.

Therefore, in a first aspect the invention relates to a composition intended for oral administration of a biological active, said composition comprising a cross-linked maltodextrin and an efficient quantity of said biological active.

The expression "maltodextrin" classically refers to the starchy material obtained by acid and/or enzymatic hydrolysis of starch. Referring to the regulatory status, the maltodextrins have a dextrose equivalent (DE) of 1 to 20.

Preferably, the maltodextrin useful to the invention has a DE chosen in the range of 5 to 20, preferably of 10 to 20, preferably of 15 to 20. This DE is for instance equal to 17.

Preferably, the maltodextrin useful to the invention is derived from starch comprising 25 to 50% of amylose, expressed as dry weight relative to the total dry weight of said starch.

This amylose content can be classically determined by the person skilled in the art by way of potentiometric analysis of iodine absorbed by amylose to form a complex.

Preferably, the maltodextrin useful to invention is derived from a starch exhibiting an amylose content chosen within the range of 25 to 45%, preferably of 30 to 45%, preferably of 35 to 40%; these percentages being expressed in dry weight of amylose with respect to the total dry weight of starch.

It is reminded that the expression "starch" classically refers to the starch isolated from any suitable botanical source, by any technique well known to those skilled in the art. Isolated starch typically contains no more than 3% of impurities; said percentage being expressed in dry weight of impurities with respect to the total dry weight of isolated starch. These impurities typically comprise proteins, colloidal matters and fibrous residues. Suitable botanical source includes for instance legumes, cereals, and tubers. In this regard, the starch of the invention is preferably a legume starch, even more preferably a pea starch, even more preferably a smooth pea starch.

Preferably, the maltodextrin useful to the invention has a weight average molecular weight chosen within the range of 5-000 to 15 000 daltons (Da), preferably of 10 000 to 15 000 Da, preferably of 10 000 to 14 000, for instance equal to 12 000 Da.

The weight average molecular weight can in particular be determined by the person skilled in the art by liquid chromatography with detection by differential refractometer, preferably by using pullulan standards.

The maltodextrin useful to the invention is obtained by hydrolysis of starch, but might has undergone other chemical and/or physical modification, as long as it does not interfere with the desired properties, notably in term of safety and efficiency of the final cross-linked maltodextrin. However, and because it appears that it is not necessary in the present invention, the maltodextrin useful to the invention is preferably no further modified.

Suitable maltodextrins are commercially available, for instance those marketed under the name KLEPTOSE® Linecaps (ROQUETTE).

The cross-linked maltodextrin useful to the invention is obtainable by (or obtained by) reacting a maltodextrin with a cross-linking compound. The cross-linking compound typically is polyfunctional, i.e. the cross-linking compound comprises at least 2 reactive functions. Preferably, the cross-linking compound is bifunctional. Typically, in the instant invention, the reactive functions have a carbon subjected to nucleophilic attack, i.e. having a partial positive charge.

Preferably, the cross-linking compound of the invention is selected from dianhydrides. The cross-linking compound of the invention is even more preferably pyromellitic dianhydride.

Preferably, the cross-linked maltodextrin of the invention comprises the following pattern:

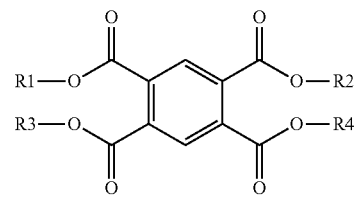

wherein R1, R2, R3, and R4 are independently selected from a hydrogen atom or a anhydroglucose unit of a maltodextrin, the number or said anhydroglucose units being at least equal to 2 in said pattern. Preferably, the number of said anhydroglucose units is equal to 2, i.e. 2 of groups R1 to R4 are hydrogens and 2 of groups R1 to R4 are anhydroglucose units.

This cross-linked maltodextrin can in particular be obtained by reacting a maltodextrin with pyromellitic dianhydride. In general, when using such cross-linking compound, then R1 and R3 are not both anhydroglucose units, and R2 and R4 are not both anhydroglucose units.

Preferably for the reaction of cross-linking, the molar ratio between the cross-linking compound and the anhydroglucose units of said maltodextrin is selected in the range of 0.1 to 10.0, more preferably of 0.1 to 5.0, still more preferably of 0.1 to 1.0, even still more preferably of 0.5 to 0.7. It is for instance equal to 0.6, that is to say that 0.6 moles of cross-linking compounds are used by mole of anhydroglucose unit.

More specifically, the cross-linked maltodextrin of the invention preferably is obtainable by (or obtained by) a process comprising the following steps:

a) preparing the solution of a maltodextrin, said maltodextrin being preferably like described before;
b) adding at least one cross-linking compound, said cross-linking compound being preferably like described before;
c) obtaining the cross-linked maltodextrin.

Preferably, the cross-linked maltodextrin of the invention, in particular the cross-linked maltodextrin intended for oral administration which is loaded with the biological active, is in the form of particles.

In that case, the average diameter of the cross-linked maltodextrin particles useful to the invention is chosen in the range of 1 to 1000 nm. It is preferably of at least 10 nm, more preferably of at least 50 nm, still more preferably of at least 100 nm. It is for instance chosen within the range of 100 to 1000 nm.

This average diameter is a hydrodynamic diameter. It can be determined by the person skilled in the art by Laser Light Scattering. It can be for instance determined according to the procedure detailed in the Examples herein after.

Preferably, the polydispersity index relative to said average diameter is lower than 1.00. This polydispersity index is in general greater than 0.05.

Preferably the cross-linked maltodextrin of the invention has a zeta potential lower than 0 mV, preferably lower than −10 mV, even lower than −20 mV. This zeta potential is in general greater than −50 mV, even greater than −40 mv.

This zeta potential can be determined by the person skilled in the art by electrophoretic mobility by dynamic light scattering, at a scattering angle of 90° at a temperature of 25° C., on a cross-linked maltodextrin suspension. It can be for instance determined according to the procedure detailed in the Examples herein after.

Preferably, the loading capacity of the cross-linked maltodextrin of the invention is of at least 1%; said percentage representing the dry weight of biological actives with respect to the total dry weight of the loaded cross-linked maltodextrin loaded with said biological actives. Preferably, this loading capacity is of at least 5%, preferably of at least 10%. This loading capacity is in general lower than 30%, even lower than 20%.

This loading capacity can be determined by the person skilled in the art by HPLC. It can be for instance determined according to the procedure detailed in the Examples herein after.

The cross-linked maltodextrin of the invention can include other compounds in its structure than the maltodextrin and the cross-linking compound useful to the invention, as long as it does not interfere with the desired properties of said cross-linked maltodextrin, in particular in terms of efficiency and safety. It is understood that by "other compounds" the inventors are not intended to include impurities, like for instance those coming from the starch used as a raw material for the preparation of the maltodextrin. Such other compounds classically are other polymers than the maltodextrin useful to the invention and/or other crosslinking compounds. They classically represent no more than 10% by weight of the total compounds used for obtaining the cross-linked maltodextrin. However more preferably, the cross-linked maltodextrin of the invention does not include other compounds in its structure than the maltodextrin and the cross-linking compound useful to the invention.

The cross-linked maltodextrin of the invention is particularly useful for the oral administration of biological actives.

According to the invention, with the definition "biological active" it is intended any kind of pharmaceutical or non-pharmaceutical biological substance to be delivered by oral route.

The expression "biological active" classically refers to actives such as proteins, nucleic acid-based actives like DNA- or RNA-based actives, cell-based actives, and virus-based actives. In particular, those actives ingredients are characterized by the fact that they are not bioavailable when administered orally, for instance because such administration route causes their degradation and/or because they are not able to cross biological barriers. In other words, these are typically the actives which are only bioavailable when administered parenterally. These actives typically are actives for which a systemic effect is desired. Such active ingredients, when they are ingested as is, typically (i) are degraded through the gastro-intestinal tract (GIT), for instance because of the low pH of the stomach, or because of enzymatic degradation, and/or (ii) are not able to cross the (GIT) barrier, for instance because of their size and/or polarity.

Preferably, the biological active according to the invention is a protein. Within the context of the invention, the term "protein" is broadly defined, as conventionally understood by the one skilled in the art. This covers in particular the proteins regardless the way they are manufactured and regardless their number of subunits. This also covers fragments of proteins, peptides and oligopeptides. They may be native proteins, recombinant proteins, or fusion proteins. The proteins of the invention preferably are composed of at least 5 amino acids, preferably at least 10 amino acids, preferably at least 20 amino acids. It is understood that the protein useful to the invention, when it comes from natural product like for example from a plant, is usually an isolated protein.

The active protein of the invention is preferably an active protein intended for pharmaceutical, veterinary, cosmetic, food or nutraceutical field. It is preferably selected from pharmaceutical proteins, for instance from enzymes, cytokines, hormones, growth factors, plasmatic factors, vaccines, antibodies. Preferably, the pharmaceutical protein useful to the invention is insulin or a pharmaceutically active derivative thereof, preferably insulin.

In a further aspect therefore the invention relates to a composition intended for oral administration of a biological active, said composition comprising a cross-linked maltodextrin and an efficient quantity of said biological active for use as a medicament In the case wherein the biological active is preferably insulin and/or a pharmaceutically active derivative thereof, the invention refers also to a composition intended for oral administration of insulin and/or of a pharmaceutically derivative thereof, said composition comprising a cross-linked maltodextrin and an efficient quantity of insulin and/or of a pharmaceutically derivative thereof for use in the prevention or in treatment of diabetes, preferably of type-1 diabetes and/or of gestational diabetes.

The uses according to the invention encompass pharmaceutical or non-pharmaceutical uses. This will essentially depends on the biological active concerned and/or on the condition to be treated and/or prevented by said biological active.

The instant invention therefore relates to a composition intended for oral administration of a biological active comprising a cross-linked maltodextrin and an efficient quantity of said biological active.

Preferably, the cross-linked maltodextrin is like described before in the preferred embodiments.

Preferably, the biological active is like described before in the preferred embodiments. It is preferably insulin and/or a pharmaceutically active derivative of thereof.

Preferably, the composition of the invention is a medicament, preferably for the treatment or prevention of diabetes, preferably of type-1 diabetes and/or of gestational diabetes. It is even more preferably for the treatment of diabetes, preferably of type-1 diabetes and/or of gestational diabetes.

In the composition of the invention, the biological active is advantageously loaded in the cross-linked maltodextrin.

For performing the loading, the cross-linked maltodextrin of the invention can be used in the liquid state, in the solid state or in the semi-solid state. For instance, the cross-linked maltodextrin is mixed with a small amount of water to allow obtaining a gel. This gel is then mixed, by kneading and/or mixing, with the biological active to be loaded, in a powder state or in a dissolved state in an appropriate solvent. Alternatively, the loaded cross-linked maltodextrin can be easily obtained by adding the selected amount of cross-linked maltodextrin with an excess of guest biological active dissolved in suitable solvent, after stirring overnight at room temperature. The loading occurs and it is recovered by simply filtration under vacuum.

The invention thus further relates to a method, for the preparation of a composition according to the invention, comprising a step of loading the cross-linked maltodextrin useful to the invention, with an efficient quantity of a biological active.

The invention also relates to a method for treating an individual, comprising oral administration of a composition according to the invention.

Preferably, the method is for the treatment or prevention of diabetes, more preferably of type-1 diabetes and/or of gestational diabetes. It is even more preferably for the treatment of diabetes, preferably of type-1 diabetes and/or of gestational diabetes.

Preferably, the method is for treating an individual suffering for diabetes, preferably of type-1 diabetes and/or of gestational diabetes.

The invention will be better understood in view of the following examples, which are intended to be illustrative and not restrictive.

EXAMPLES

A. Delivery Systems Synthesis

1. Delivery System According to the Invention (MDX-PYR): Maltodextrin Cross-Linked by Pyromellitic Dianhydride (PMDA) in a Molar Ratio PDMA/Anhydroglucose Units of 0.57

Into a round bottom flask set in a water bath and magnetic stirrer, 40 mL of DMSO with 9.78 g of dehydrated KLEPTOSE® Linecaps (maltodextrin deriving form smooth pea starch, having an amylose content of 35-45%, a DE of 17, and a weight average molecular weight of 12 000 Da) were introduced and stirred until a colorless homogeneous solution was obtained. 10 mL of triethylamine were added into the solution then 7.52 g of pyromellitic dianhydride. A dark amorphous solid-like gel was formed and left overnight to solidify. Using a mortar and pestle the cross-linked maltodextrin was ground and washed several times with distilled water then acetone in Buchner, dried then extracted with acetone in a Soxhlet at 60-70° C. for 48 hours. Finally the clean powder was dried, ground and collected.

A suspension of MDX-PYR particles thus obtained was prepared using a top down method. The MDX-PYR was suspended in saline solution (NaCl 0.9% w/v) at the concentration of 10 mg/mL under stirring at room temperature. The suspension was then dispersed for 10 minutes using a high shear homogenizer (Ultraturrax®, IKA, Konigswinter, Germany). The suspension was then subjected to high pressure homogenization for 90 minutes at a back-pressure of 500 bar (EmulsiFlex C5, Avastin, USA). Finally, the MDX-PYR suspension was purified by dialysis to eliminate potential synthesis residues (Spectrapore, cellulose membrane, cutoff 12000 Da) and finally stored at −4° C.

2. Comparative Delivery System (BCD-PYR): Cyclodextrin Cross-Linked by Pyromellitic Dianhydride (PMDA) in a Molar Ratio PDMA/Anhydrglucose Units of 0.57

Comparative cross-linked beta-cyclodextrin BCD-PYR was prepared according to Example 1 of Italian patent application ITBO20120710.

B. Delivery System Characterization

The delivery systems obtained according to section A. above were characterized for the following features: average diameter, polydispersity index, zeta potential, pH value.

pH was evaluated at room temperature using a pH meter (Orion model 420A), on the suspension comprising 10 mg/mL of the delivery system.

For the determination of the average diameter and polydispersity index and zeta potential, the suspension comprising 10 mg/mL of the delivery system was first diluted with filtered (0.22 μm) distilled water, using a dilution factor of 1/30 by volume.

The average diameter and polydispersity index were determined by Laser Light Scattering (90plus Instrument, Brookhaven, NY, USA) on the diluted suspension of the delivery system. The analyses were performed at a scattering angle of 90° at a temperature of 25° C., with a refractive index of 1.330 and a viscosity of 0.890 cPs.

Zeta potential was determined on the diluted suspension of the delivery system by electrophoretic mobility using the same instrument. The analyses were performed at a scattering angle of 90° at a temperature of 25° C. For zeta potential determination, samples of diluted delivery system formulations were placed in the electrophoretic cell, where an electric field of 15V/cm was applied.

Results are shown in Table 1.

TABLE 1

|  | BCD-PYR | MDX-PYR |
|---|---|---|
| Average diameter | <1000 nm | <1000 nm |
| Polydispersity index | <1.00 | <1.00 |
| Zeta potential | −23.82 ± 3.25 mV | −29.75 ± 2.20 mV |
| pH value | 3.50 | 4.35 |

C. Insulin Loading

1. Protocol for Insulin Loading

Insulin from bovine pancreas powder was used to prepare a 2 mg/mL solution in distilled water pH 2.3 adjusted using phosphoric acid. Insulin solution was added to pre-formed aqueous nanosuspensions in a mass ratio insulin solution:nanosuspension of 1:5. The mixture was stirred at room temperature for 30 minutes to be incorporated, centrifuged then supernatant separated from sediment collected and lyophilized for future used 2. Evaluation a. Loading Capacity The loading capacity was determined from freeze-dried insulin loaded samples. Briefly, a weighted amount of 2-3 mg of freeze-dried delivery system loaded with insulin was disperses in 5 mL of distilled water. Sonication (15 minutes, 100 W) and centrifugation treatments were performed so as to allow the release of insulin from the delivery system. Then the supernatant was analyzed for the quantitative determination of insulin.

The quantitative determination of insulin was carried out by High Performance Liquid Chromatography analysis, HPLC pump (Perkin Elmer 250B, Waltham, MA) equipped with a spectrophotometer detector (Flexar UV/Vis LC, Perkin Elmer, Waltham, MA). An analytical column C18 (250 mm×4.6 mm, ODS ultrasphere 5 µm; Beckman Instruments, USA) was used. The mobile phase consisted of a mixture of 0.1M sodium sulfate in distilled water and acetonitrile (72:28 v/v) filtered through a 0.45 µm nylon membrane and ultrasonically degassed prior to use. Ultraviolet detection was fixed at 214 nm and the flow rate was set to 1 ml/min. The insulin concentration was calculated using external standard method from standard calibration curves. For this purpose, 1 mg of Insulin was weighted, placed in a 10 mL volumetric flask, and dissolved in distilled water pH 2.3 adjusted by phosphoric acid to obtain a mother solution. This solution was then diluted using the mobile phase and a series of standard solutions were prepared, consequently injected into the HPLC system. Linear calibration curves were obtained over the concentration range of 0.5-25 µg/mL, linear plotted with regression coefficient of 0.999.

The loading capacity of the delivery systems was calculated as follows:

[weight of insulin/weight of freeze dried delivery system]×100.

Results are shown in Table 2.

TABLE 2

|  | BCD-PYR + insulin | MDX-PYR + insulin |
|---|---|---|
| Loading capacity | 14.32% | 10.31% | b. In Vitro Drug Release Kinetics

In vitro drug release experiment was conducted in a multi-compartment rotating disc (a diffusion cell system comprising a donor chamber separated by a membrane from the receiving compartment), constituted from several donor cells on one side separated by cellulose membrane (Spectrapore, cut-off 12000-14000 Da) from the receiving cells on the other side. Insulin-loaded delivery systems were placed in the donor cell (1 mL). The receiving cells were filled by phosphate buffered saline PBS solutions pH 1.2 and pH 6.8 separately. In vitro release studies were carried out during 6 hours, receiving phase was withdrawn at regular intervals and replaced with the same amount of new PBS solution. The sampling times investigated were 0.25, 0.5, 0.75, 1, 1.5, 2, 3, 4, 5, and 6 hours. The concentration of Insulin in the withdrawn samples was later detected by HPLC.

Figure 2:
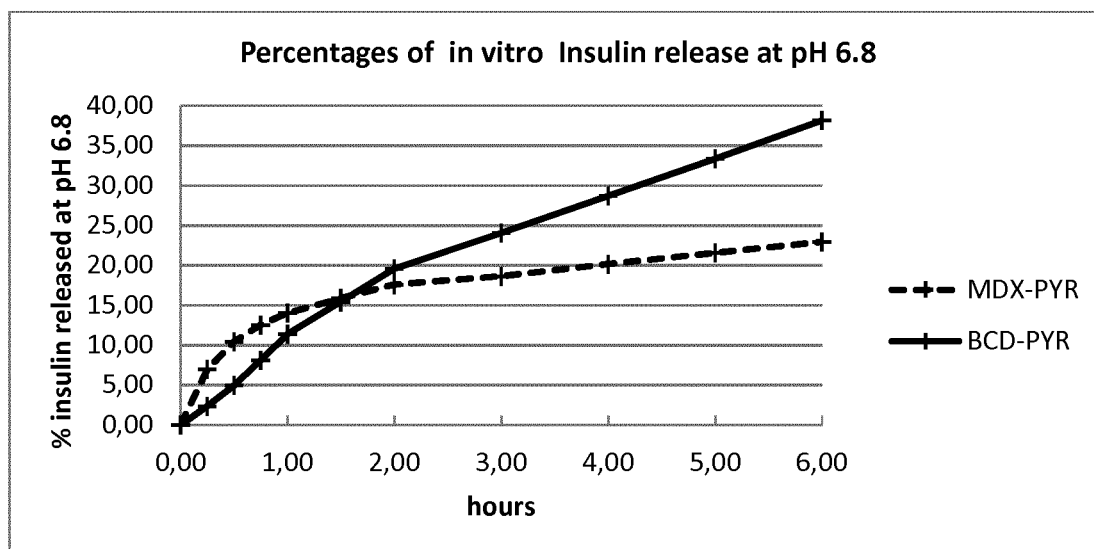
FIG. 2: Percentages of in vitro insulin released from different delivery systems at pH 6.8 over the time.

Results are shown in FIGS. 1 and 2.

Like for the delivery system of prior art, the delivery system MDX-PYR of the invention prevents the release of insulin at gastric pH (FIG. 1), whereas it allows insulin release at intestinal pH (FIG. 2). That is to say that the delivery system MDX-PYR of the invention prevents the release of insulin at a pH at which it would be hydrolyzed due to the high acidity of the stomach, and allows the release of insulin in the intestine, where insulin absorption is desired.

However, contrary to the delivery system BCD-PYR of prior art, the delivery system MDX-PYR of the invention advantageously allows slower release of insulin. That is to say that the insulin is potentially bioavailable during a longer period of time. This also means that the delivery system of the invention will less likely provoke a brutal increase of blood insulin after ingestion. That is to say that the delivery system of the invention is potentially safer, as a brutal increase of blood insulin can lead to harmful hypoglycemia.

This great potential of the delivery system of the invention was investigated and confirmed in the following in vivo experiments.

c. In Vivo Oral Administration of the Delivery Systems Loaded with Insulin

The delivery systems formulations were administrated to mice by oral gavage in the stomach. The Insulin concentration was 6 U/ml (210 mg/ml insulin) so the dose administered 30 U/kg and blood withdrawals were collected at 0, 30, 60, 120, 180 and 240 minutes. Insulin was later extracted from plasma samples using the following protocol. To each 100 µl of plasma 100 µl of PBS (pH 7.4), 50 µl of acetonitrile, 20 µl of ethyl paraben, 3 ml of dichloromethane/n-hexane (1:1 v/v) were added. The mixture was on vortex for 2 min then centrifuged at 5000 rpm for 10 min. The supernatant was transferred to a test tube to evaporate the organic phase under nitrogen flux. Later 300 µl of HCl 0.05N was added on vortex for 2 minutes. After the organic phase completely evaporated under nitrogen flux then centrifuged at 15000 rpm for 10 min. Clear supernatants were later injected in HPLC after suitable dilution.

Figure 3:
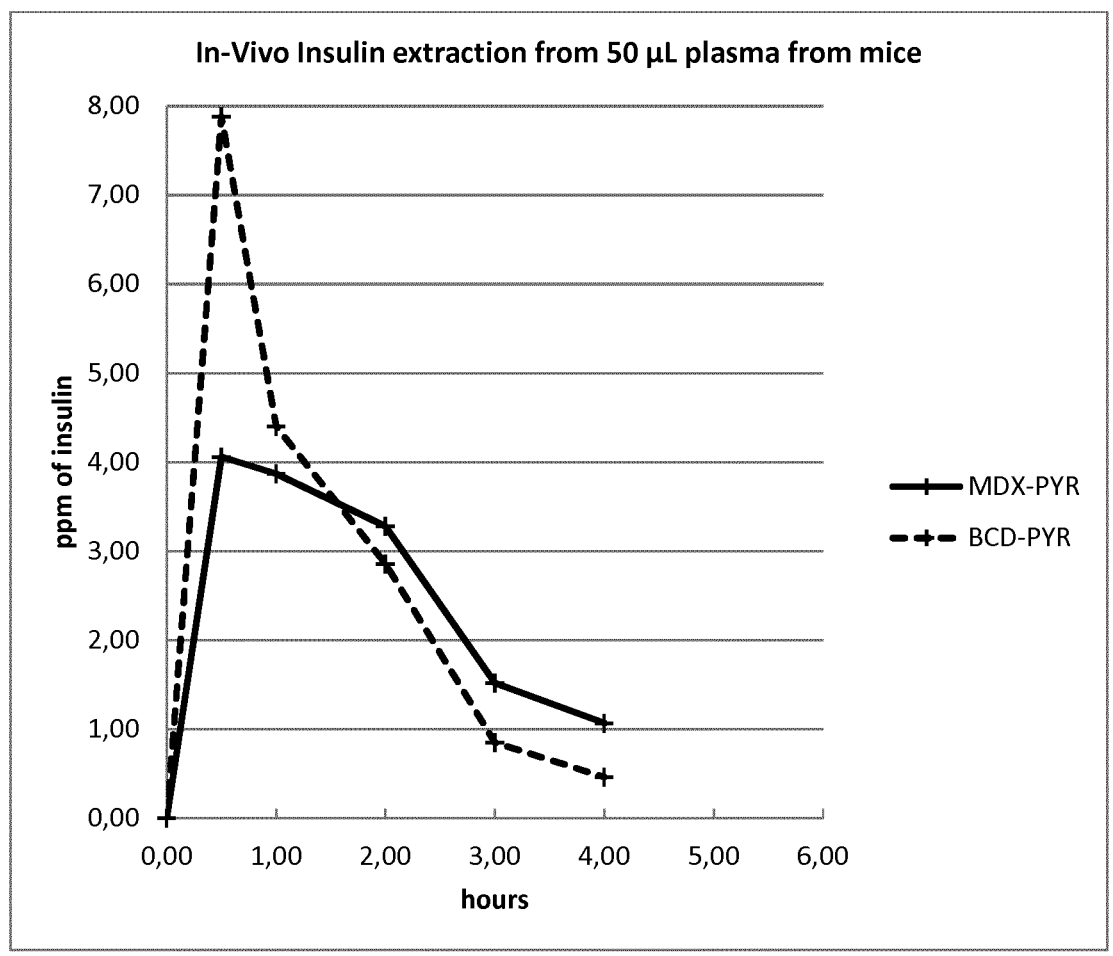
FIG. 3: In vivo blood insulin after oral administration to mice of different delivery systems loaded with insulin.

Results are shown in FIG. 3.

After oral administration of insulin-loaded cross-linked maltodextrin MDX-PYR of the invention, the blood insulin increases up to 4 ppm/50 µL of plasma, and then slowly decrease over time. On the contrary, when using the cross-linked beta-cyclodextrin BCD-PYR of prior art, the blood insulin shows a brutal increase, up to 8 ppm/50 µL of plasma, followed by a quick decrease. 4 hours after oral ingestion, the blood insulin is twice higher with the use of the delivery system of the invention.

These experiments thus confirmed the advantageous pharmacokinetic behavior brought by the delivery system of the invention. The results confirmed (i) the greater safety (lower blood insulin peak after ingestion) and (ii) the longer-lasting effect (blood insulin still high after 4 hours) associated with the use of the delivery system of the invention.

The invention claimed is:
1. A composition comprising a cross-linked maltodextrin and an efficient quantity of insulin, wherein the composition is suitable for oral administration and provides long-lasting release of the insulin in the intestine, and wherein said cross-linked maltodextrin is obtainable by reacting a maltodextrin with a cross-linking compound selected from dianhydrides.

2. The composition of claim 1, wherein said maltodextrin is derived from starch comprising amylose in the range from 25 to 50% expressed as dry weight relative to the total dry weight of said starch.

3. The composition of claim 1, wherein said dianhydride is pyromellitic dianhydride.

4. The composition of claim 1, wherein said cross-linked maltodextrin is obtainable by reacting a maltodextrin with a cross-linking compound, and wherein for the reaction of cross-linking, the molar ratio between the cross-linking compound and the anhydroglucose units of said maltodextrin is selected within the range of 0.1 to 10.0.

5. The composition of claim 1, further comprising at least one suitable excipient.

6. The composition according to claim 5, wherein the composition is a medicament or a veterinary product.

7. The composition according to claim 5, wherein the composition is selected from the group consisting of a cosmetic product, a food and a nutraceutical product.

8. A composition consisting of a cross-linked maltodextrin and an efficient quantity of insulin, wherein the composition is suitable for oral administration and provides long-lasting release of the insulin in the intestine.

9. A composition consisting of a cross-linked maltodextrin, an efficient quantity of insulin, and a suitable excipient, wherein the composition is suitable for oral administration and provides long-lasting release of the insulin in the intestine.

10. A method for the treatment of diabetes in a subject in need thereof, comprising the step of administering the composition according to claim 1 to said subject.

11. The method for the treatment of diabetes according to claim 10, wherein said diabetes is type-1 diabetes and/or gestational diabetes.

12. A method for the preparation of a composition according to claim 1, comprising a step of loading said cross-linked maltodextrin with an efficient quantity of said biological active, wherein said biological active is insulin.

13. A method comprising administering a composition of cross-linked maltodextrin and insulin as defined in claim 2, to a subject in need thereof.

* * * * *